United States Patent
Nishida et al.

(10) Patent No.: US 6,810,748 B1
(45) Date of Patent: Nov. 2, 2004

(54) METHOD FOR EVALUATING CREEP LIFETIME

(75) Inventors: Hidetaka Nishida, Higashihiro Shima (JP); Hiroshi Yamaguchi, Hiroshima (JP); Nobuaki Kosako, Hiroshima (JP)

(73) Assignee: The Chugoku Electric Power Co., Inc., Hiroshima (JP)

( * ) Notice: Subject to any disclaimer, the term of this patent is extended or adjusted under 35 U.S.C. 154(b) by 0 days.

(21) Appl. No.: 10/344,638

(22) PCT Filed: Aug. 16, 2000

(86) PCT No.: PCT/JP00/05470

§ 371 (c)(1),
(2), (4) Date: Jul. 1, 2003

(87) PCT Pub. No.: WO02/14835

PCT Pub. Date: Feb. 21, 2002

(51) Int. Cl.[7] ............................................. G01N 3/00
(52) U.S. Cl. ............................. 73/788; 73/835; 356/32
(58) Field of Search ...................... 73/789–798, 788, 73/835, 799, 762, 800; 356/32

(56) References Cited

U.S. PATENT DOCUMENTS

| | | | | |
|---|---|---|---|---|
| 4,875,170 A | * | 10/1989 | Sakurai et al. | 73/799 |
| 4,907,457 A | * | 3/1990 | Nishimura et al. | 73/787 |
| 5,045,283 A | * | 9/1991 | Patel | 422/56 |
| 2003/0062397 A1 | * | 4/2003 | Komai et al. | 228/103 |

OTHER PUBLICATIONS

K. Iwamoto, "Latest Trend of Non–Destructive Test for Boiler", Thermal Nuclear Power Generation, vol. 48, No. 8, Aug. 1997, pp. 14–24.

I. Nonaka et al, "Life Assessment Techniques of Power Boiler Plants", Ishikawajima–Harima Technical Report, vol. 32, No. 5, 1992, pp. 313–318.

K. Kikuchi et al, "A Proposal of Grain Boundary Damage Parameter", Journal of the Society of Materials Science, vol. 44, No. 505, 1995, pp. 1244–1248.

Manual on Evaluation of Creep and Creep–Fatigue Damage/Lives by Replication Method, The Iron and Steel Institute of Japan, 1991, pp. 1–14.

"Technology for Evaluating Future Lifetime of Power Plant and Structure", edited by the Japan Society of Mechanical Engineers, 1992, pp. 89–93.

T. Ejima et al, "Initiation of Inner Small Crack in High–Temperature Creep–Fatigue in Type 304 Stainless Steel", Proceedings of the 32nd Symposium on Strength of Materials at High Temperatures, 1994, pp. 94–98.

N. Tada et al, "Measurement of the Distribution of Cavities on Grain Boundary and Evaluation of Damage Parameters of SUS304 Stainless Steel under Creep–Fatigue Condition", Journal of The Society of Materials Science, vol. 46, No. 1, 1997, pp. 39–46.

N. Tada et al, "Physical Meaning of Creep Damage Parameters Evaluated from Distribution of Grain Boundary Cavities on Cross–Section", Journal of The Soceity of Materials Science, vol. 45, No. 1, 1996, pp. 110–117.

* cited by examiner

*Primary Examiner*—Edward Lefkowitz
*Assistant Examiner*—Alandra Ellington
(74) *Attorney, Agent, or Firm*—Mattingly, Stanger & Malur, P.C.

(57) ABSTRACT

A part where a creep void is recognized is observed at an arbitrary magnification by a scanning electron microscope, an optical microscope, and a laser microscope, and the maximum value of creep void crystal grain boundary occupancy is measured in the field of view. The maximum value is applied to a a master curve corrected from the results of a test of simulating an actual machine and a test piece of actual machine size, taking account of internal damage of the machine. Thus the creep lifetime consumption rate of a member is estimated easily with high accuracy.

1 Claim, 15 Drawing Sheets

METHOD FOR EVALUATING CREEP LIFETIME

TECHNICAL FILED

The present invention relates to a method of evaluating a creep life consumption rate of an equipment member, which uses a maximum value of occupation ratio of creep voids at a crystal grain boundary and considers a correspondence of an actual life to the life on a surface, in order to evaluate the creep life consumption rate and a future lifetime of a member having been subjected to creep deterioration.

BACKGROUND ART

In order to steadily operate a thermal electric power plant for a long period of time, it is necessary to accurately know the life of equipment. For 80 percent or more of commercial thermal power generation units now located in Japan, the accumulative operation time exceeds 100,000 hours, and for about 20 percent of them, the accumulative operation time exceeds 200,000 hours (Reference 1: Keiichi Iwamoto, Thermal Nuclear Power Generation, 48–8 (1997), 14). Therefore, it is important from the viewpoint of preventive maintenance as well as cost reduction that diagnosis of the future lifetime of a boiler etc. of aged thermal power generation unit be performed at the time of regular inspection, the state of equipment be accurately grasped, and proper repairs be made.

In weld portions of a high-temperature member of thermal power generation boiler, minute pores called creep voids (hereinafter referred to as voids) are developed in the metallographic structure due to the progress of creep damage caused by the long-term use. These voids grow and connect with each other to form a microcrack of one grain boundary length. Subsequently, the formed microcracks propagate and coalesce repeatedly, which leads to breakage of the whole of the member.

At present, the creep life is evaluated by non-destructive inspection, which is made by grinding and corroding the material surface. The non-destructive inspection method includes the parameter method using a replica (Reference 4: The Iron and Steel Institute of Japan, Creep and creep fatigue damage manual using replica method "Result reports of high-temperature strength WG, Reliability evaluation technical department" (separate-volume manual), (1991), 1) such as the A parameter method, structure comparison method, void area ratio method (Reference 2: for example, Isamu Nonaka, Keisuke Sonoya, Masashi Nakadai, Hiroshi Yoneyama, and Masaki Kitagawa, Ishikawajima-Harima Technical Report, 32–5(1992), 313), void surface density method, and grain boundary damage method (Reference 3: Kenji Kikuchi and Yoshiyuki Kaji, Material, 44–505(1995), 1244), and the ultrasonic noise energy method and the ultrasonic spectroscopy method (Reference 5: edited by The Japan Society of Mechanical Engineers, Technology for evaluating future lifetime of power plant and structure, (1992), 89, published by Gihodo Shuppan).

In the evaluation method in which attention is given to the voids at the grain boundary, it has been clarified that the void occupation ratio on the grain boundary line (Reference 6: Tsuneyuki Ejima, Syu, Ryuichi Ohtani, Takayuki Kitamura, and Naoya Tada, 32nd High-temperature Strength Symposium Procedings, (1994), 94) has a clear physical meaning as a damage parameter (Reference 7: Naoya Tada, Satoshi Fukuda, Takayuki Kitamura, and Ryuichi Ohtani, Material 46–1, (1997), 39;

Reference 8: Naoya Tada, Takayuki Kitamura, and Ryuichi Ohtani, Material 45-1, (1996), 110).

That is, the evaluation of creep life consumption rate and future lifetime has so far been made by the void area ratio in the unit area range in a predetermined region (void area ratio method), or by the ratio of grain boundary at which voids are developed to the number of intersections of a straight line and a grain boundary (A parameter method), the straight line being drawn in the direction of the principal stress in a predetermined region.

However, the above-described conventional methods have problems with the life evaluation system of equipment member; for example, the evaluation is too conservative when the creep life consumption rate obtained by the conventional method is compared with the creep life consumption rate obtained by a destructive test of the same portion, and the mechanism of actual creep rupture is not evaluated directly.

Also, in some cases, the stress direction is considered. Since the member of equipment used actually (hereinafter referred to as actual equipment) has a multiaxial stress field, the conventional methods are impractical. Also, since many evaluation points must be set, much time is required for the quantification of void development state and the estimation of creep life.

DISCLOSURE OF THE INVENTION

The present invention has been achieved in consideration of the above circumstances, and an object thereof is to solve the above problems and to provide a method of estimating the creep life consumption rate with high accuracy.

To solve the above problems, the present invention is characterized in that a maximum creep void/grain boundary ratio (MB) of actual equipment member is determined by using a master curve corrected considering the size etc. of equipment member from the result obtained by a rupture test piece of actual equipment member size and a test piece in which the actual equipment member is simulated, by which the creep life consumption rate of the whole of equipment member can be estimated with high accuracy.

The maximum creep void/grain boundary ratio (MB) is expressed by Equation 1.

Maximum creep void/grain boundary ratio (MB)

$$\text{Maximum creep void/grain boundary ratio (MB)} = \underset{\alpha=1}{\overset{m}{\text{MAX}}} \left[ \frac{\sum_{i=1}^{n} l_{\alpha i}}{L_\alpha} \right]$$

In Equation 1, $L_\alpha$ is the total length of one grain boundary at which a creep void exists, n is the number of creep voids at a grain boundary having the total length of $L_\alpha$ of one grain boundary at which the creep voids exist, m is the number of grain boundaries at which a creep void exists, and $1_\alpha$ is a void length which is the length of the intersection of a grain boundary and a void along the grain boundary. The maximum creep void/grain boundary ratio (MB) will be referred to more simply as "maximum void/grain boundary ratio (MB)" in some cases.

Also, the present invention is characterized in that in order to obtain the correspondence of the creep life of equipment member to the creep life consumption rate of member surface, an equipment member creep life consumption rate a at the time when the maximum creep void/grain boundary ratio (MB)=1 is determined by an acceleration creep test or a creep analysis, and the equipment member creep life consumption rate α is used.

BEST MODE FOR CARRYING OUT THE INVENTION

Tests in accordance with the present invention will now be described with reference to the accompanying drawings.

[Test 1]

Figure 1:
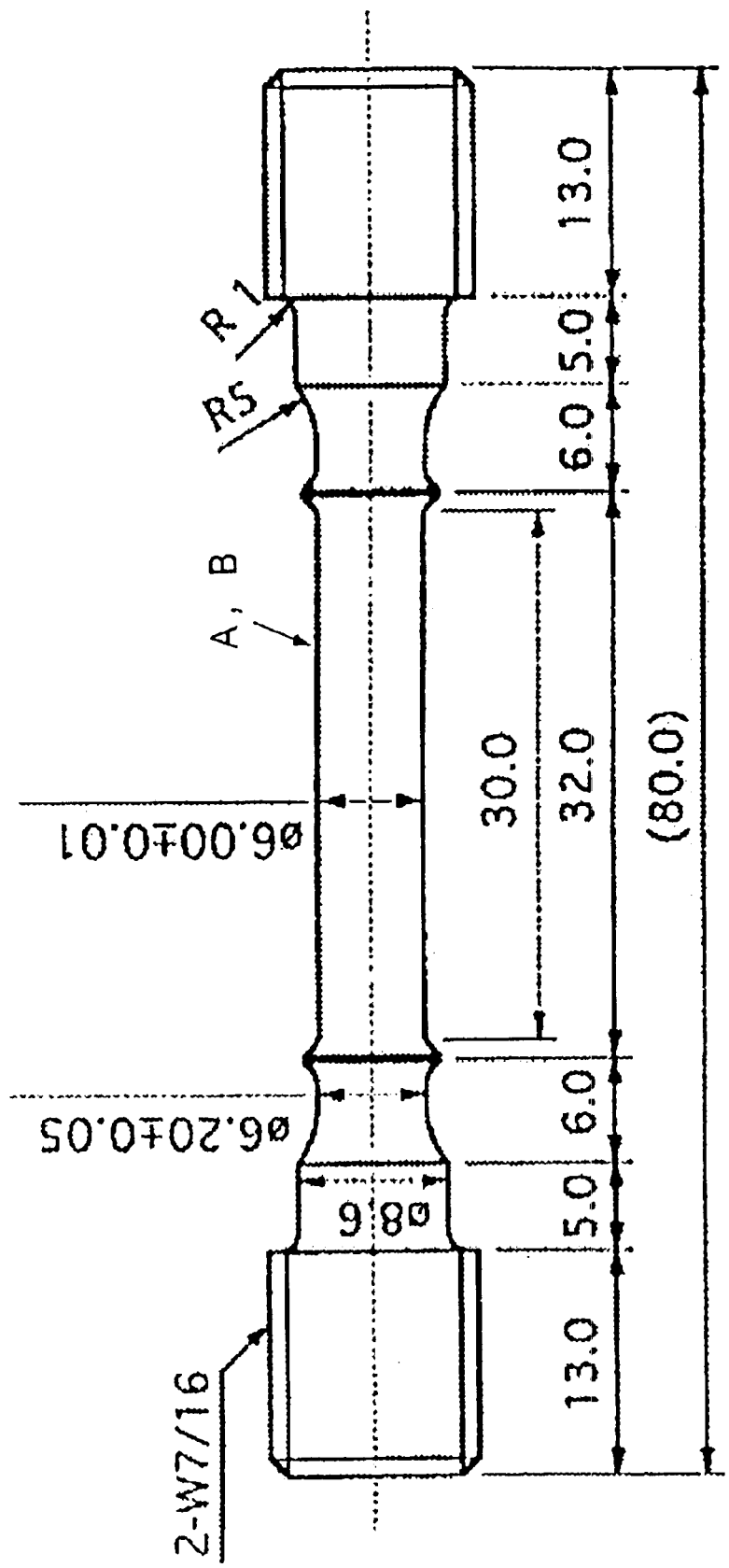
FIG. 1 is a view showing a test piece used for a creep interruption test in a void growth behavior verification test using a uniaxial creep rupture test piece of test 1 in accordance with the present invention.

Avoid growth behavior verification test using a uniaxial creep rupture test piece of test 1 for finding the creep life evaluation method in accordance with the present invention is conducted to grasp the development, growth behavior, and distribution of voids in the process of creep damage. In this test, a reproduced material (2.25Cr-1Mo steel) of a coarse grain region of weld heat affected zone (hereinafter referred to as a coarse grain Haz) was prepared, and a creep interruption test was conducted by using a test piece shown in FIG. 1. The test was conducted by using a test piece A (903K, 60.8 MPa, rupture time tr=1774 hr) and a test piece B (843K, 123.5 MPa, rupture time tr=3396 hr). Regarding interruption time t, interruption was effected at times of 800 hr (creep life consumption rate t/tr=0.45), 1200 hr (t/tr=0.68), 1608 hr (t/tr=0.91) and 1774 hr (t/tr=1.0) for the test piece A, and at times of 816 hr (t/tr=0.24), 1190 hr (t/tr=0.35), 1596 hr (t/tr=0.46), and 3396 hr (t/tr=1.0) for the test piece B.

Void observation was made by using a scanning electron microscope (hereinafter referred to as a SEM) by dividing the test piece longitudinally into two pieces. Regarding the observation point, a position in which relatively many voids are developed was observed continuously with about 100 fields of view at a magnification of ×1000.

[Test 2]

Figure 2:
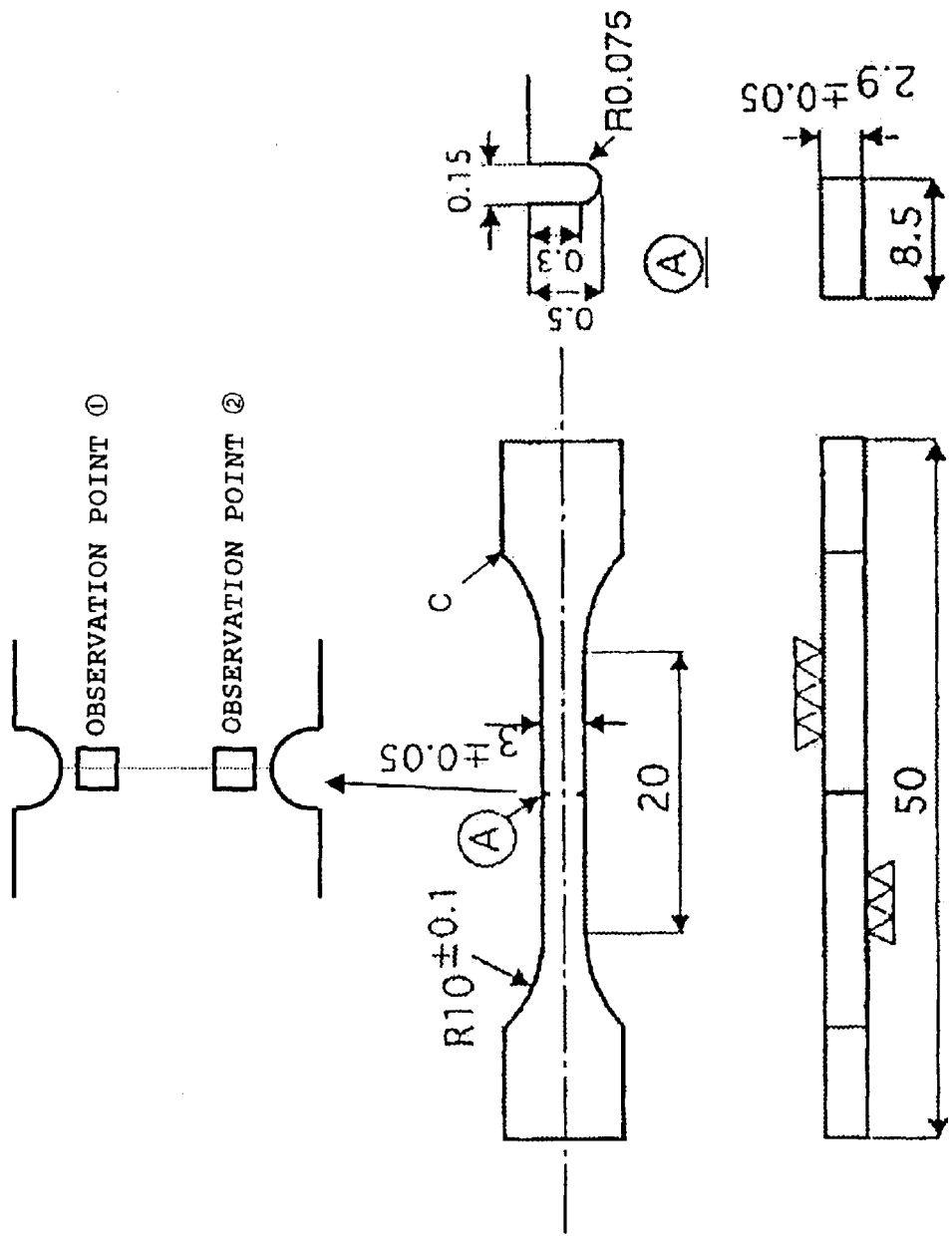
FIG. 2 is a view showing a test piece used for a creep damage continuous observation test of test 2 in accordance with the present invention.

In a creep damage continuous observation test of test 2 for finding the creep life evaluation method in accordance with the present invention, in order to grasp a process from the growth and connection of voids to the formation of microcrack, a creep test was conducted using a test piece C (2.25Cr-1Mo steel) shown in FIG. 2 (903K, 68.6 MPa, tr=136 hr) under a SEM to which a loading device and a heating coil are attached (hereinafter referred to a SEM servo testing machine), and at the same time, the development and growth of voids at the crystal grain boundary on the surface of test piece was observed continuously.

The test piece was taken so that the heat affected zone of welded joint portion lies in the center of the test piece, and a U-shaped notch was formed at both sides in the center of the heat affected zone. The surface of test piece was etched so that the crystal grain boundary could be discriminated. The test time was set at time such that the observation does not become difficult due to the oxidation of the surface of test piece (about 100 hr).

The observation was made at a magnification of ×1000 at observation points ① and ② on a line connecting notch bottoms A at both sides. The observation was made at proper intervals until the test piece was broken. At the observation point ①, the interruption time was 15 hr (t/tr=0.11), 36 hr (t/tr=0.26), 59 hr (t/tr=0.43), 82 hr (t/tr=0.60), 106 hr (t/tr = 0.78), and 118 hr (t/tr=0.87). At the observation point ②, the interruption time was 58 hr (t/tr=0.43), 87 hr (t/tr=0.64), 105 hr (t/tr=0.77), and 118 hr (t/tr=0.87).

[Test 3]

Figure 3:
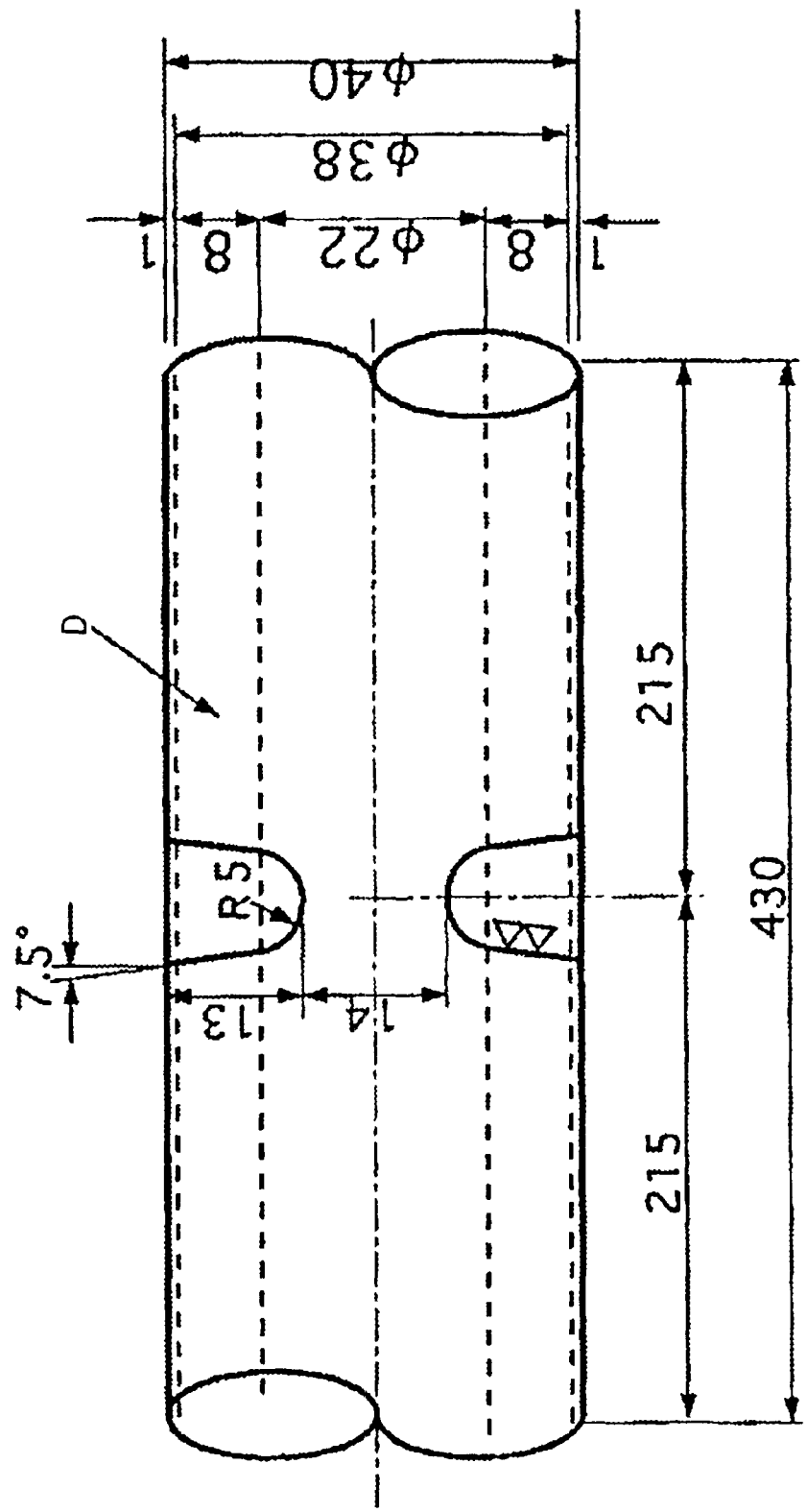
FIG. 3 is a view showing a hollow round bar used for an internal pressure creep rupture test of circumferential welded joint portion of a pipe of test 3 in accordance with the present invention.

In an internal pressure creep rupture test of circumferential welded joint portion of a pipe (pipe internal pressure creep test) of test 3 for finding the creep life evaluation method in accordance with the present invention, in order to grasp a process of void development and growth in an actual equipment member, an internal pressure creep rupture test using as a test piece D (40 dia.×8 t×1430) welded joint pipe (2.25Cr-1Mo steel), which was obtained by performing circumferential welding on a solid round bar shown in FIG. 3 and by boring a hole in the center thereof (hereinafter referred to as a pipe internal pressure creep rupture test. 903K, circumferential stress by the Equation of average diameter 61.3 MPa, tr=4131 hr) was conducted.

The weld portion of test piece was prepared by shielded metal arc welding of 1 to 4 layers, and was subjected to heat treatment for 993K×1.3 hours after welding. The detailed welding conditions were determined by simulating the manufacturing conditions of actual equipment to the utmost. In the test, the test piece was heated in an electric furnace, and pressurized water was poured to turn to high-pressure steam, by which an internal pressure was applied. The test was interrupted, and voids were observed at the time of interruption. The interruption was effected at time of 2010 hr (t/tr=0.49), 3000 hr (t/tr=0.73), and 4000 hr (t/tr=0.97).

[Test 4]

Figure 4:
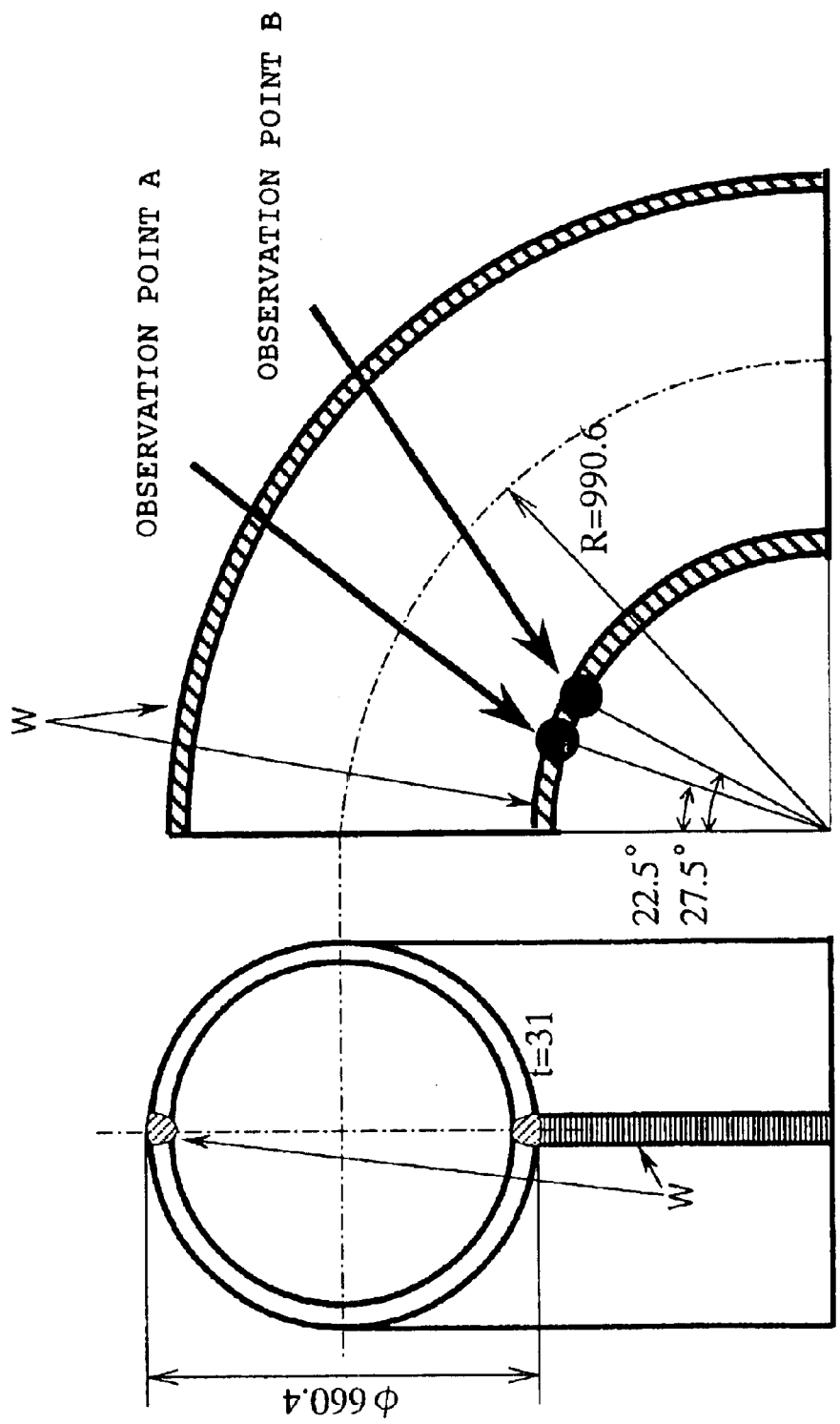
FIG. 4 is a view showing a waste material of high-temperature reheat steam pipe for a thermal electric power plant, which is used for an internal pressure creep rupture test of lengthwise welded joint portion of a high-temperature reheat steam pipe elbow in test 4 in accordance with the present invention.

In an internal pressure creep rupture test of lengthwise welded joint portion of a high-temperature reheat steam pipe elbow (actual equipment acceleration test) of test 4 for finding the creep life evaluation method in accordance with the present invention, in order to grasp a process in which voids are developed and grow in a large member of actual equipment, connect together and breakage occurs finally, an internal pressure creep rupture test (923K, internal pressure 3.0MPa, maximum principal stress in the center of elbow abdomen 39.2 MPa, tr=2950 hr) was conducted using a waste material of high-temperature reheat steam pipe for a thermal electric power plant (2.25Cr-1Mo steel, creep life consumption rate (t/tr) at the time of disposition was about 0.5) shown in FIG. 4 as an actual equipment test specimen (660.4 dia.×31 t). In FIG. 4, reference character W denotes a weld portion, and A and B denote observation points of the weld portion W.

In the test, after the test specimen was surrounded by a plate heater and was heated, pressurized water was poured into the test specimen to turn to high-pressure steam, by which an internal pressure was applied. The test was interrupted, and a replica was taken from the surface of the welded joint portion at the time of interruption, and voids were observed by using a SEM. The test specimen was an elbow that was manufactured by bending two plates and welding them longitudinally by submerged arc welding. The interruption was effected at creep life consumption rates (t/tr) of about 0.5, 0.7, 0.8 and 0.9.

[Test 5]

In a uniaxial creep rupture test of welded joint portion of a thermal electric power plant waste material (actual equipment waste material test) of test 5 for finding the creep life evaluation method in accordance with the present invention, in order to grasp the creep life consumption rate of actual equipment member and the development and growth form of voids at that time, an uniaxial creep rupture test using actual equipment waste material (hereinafter referred to as an actual equipment waste material test) and observation of voids using a replica were carried out. First, the creep rupture test for calculating the life consumption rate of actual equipment member was conducted.

Figure 5:
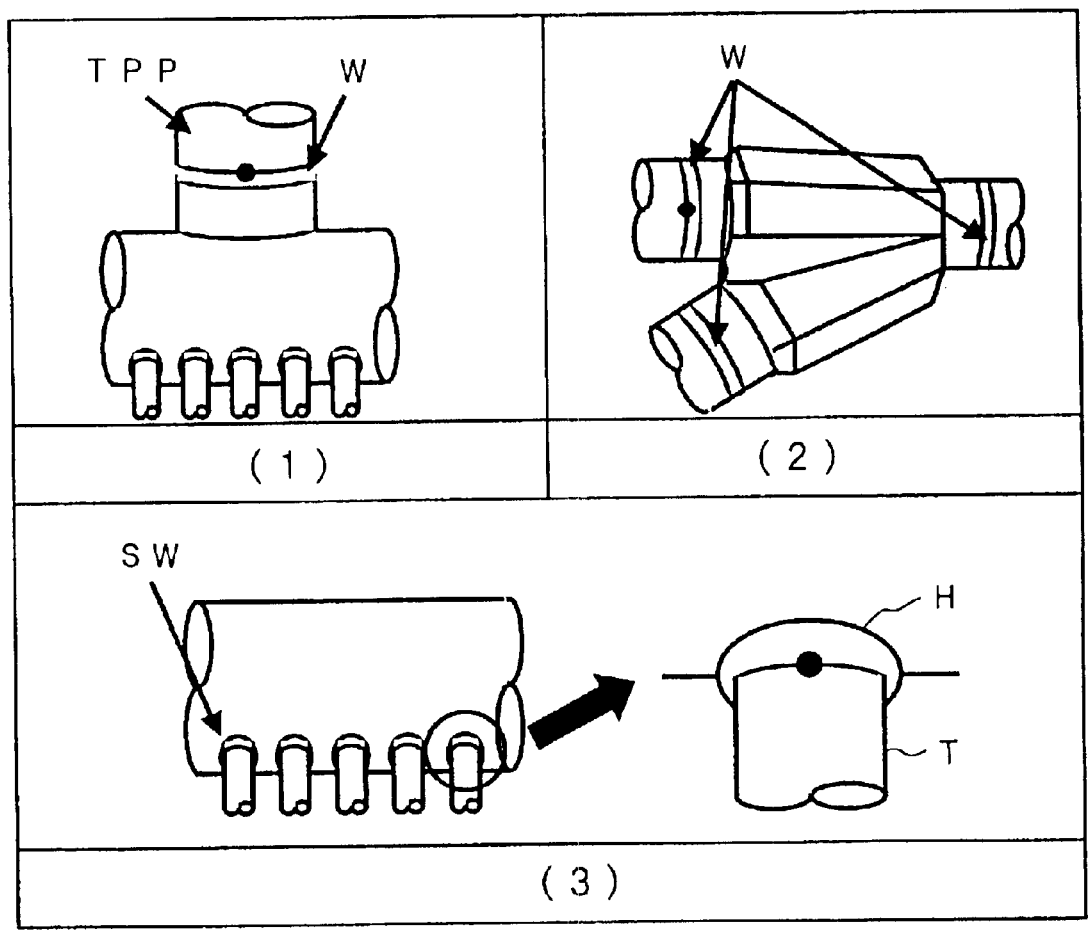
FIG. 5 is a view showing a position from which a test piece is taken of each waste material used for a uniaxial creep rupture test of welded joint portion of a thermal electric power plant waste material of test 5 in accordance with the present invention.

A test piece was taken from a section near the surface of a portion in which a void was recognized by the replica examination of the actual equipment surface. The creep rupture test was conducted in an inert gas atmosphere by using a round bar test piece with a diameter of 10 mm and a gauge length of 50 mm for the circumferential weld portion and a miniature creep round bar test piece with a diameter of 2 mm for the header stub weld portion. Also, a replica of actual equipment section (near the surface) was taken from the portion from which the creep rupture test piece was taken, and voids were observed by using a SEM. The test piece was taken from a circumferential weld portion of superheater header in thermal electric power plant, a circumferential weld portion of reheat Y piece, and a weld portion of header stub of reheater. FIG. 5 shows the position from which the test piece of each waste material was taken, and Table 1 gives the service conditions of each waste material. In FIG. 5, (1) shows an SH header T piece pipe, (2) shows a RHY piece pipe, and (3) shows an RH header stub. The ● mark indicates the position from which the test piece was taken. Reference character W denotes a weld portion, SW denotes a stub weld portion, TPP denotes a T piece pipe, H denotes a header, and T denotes a tube.

TABLE 1

|  | SH header T piece pipe | RHY piece pipe | RH header |
|---|---|---|---|
| Operation temperature (K) | 842 | 814 | 814 |
| Pressure (Mpa) | 16.97 | 3.19 | 3.19 |
| Material | STBA22 | STBA24 | STBA22 |
| Operation time (hr) | 202164 | 202164 | 202164 |
| Number of starts and stops | 402 | 402 | 402 |

The results of the above-described tests are shown in FIGS. 6 to 11.

[Result of Test 1]

Figure 6:
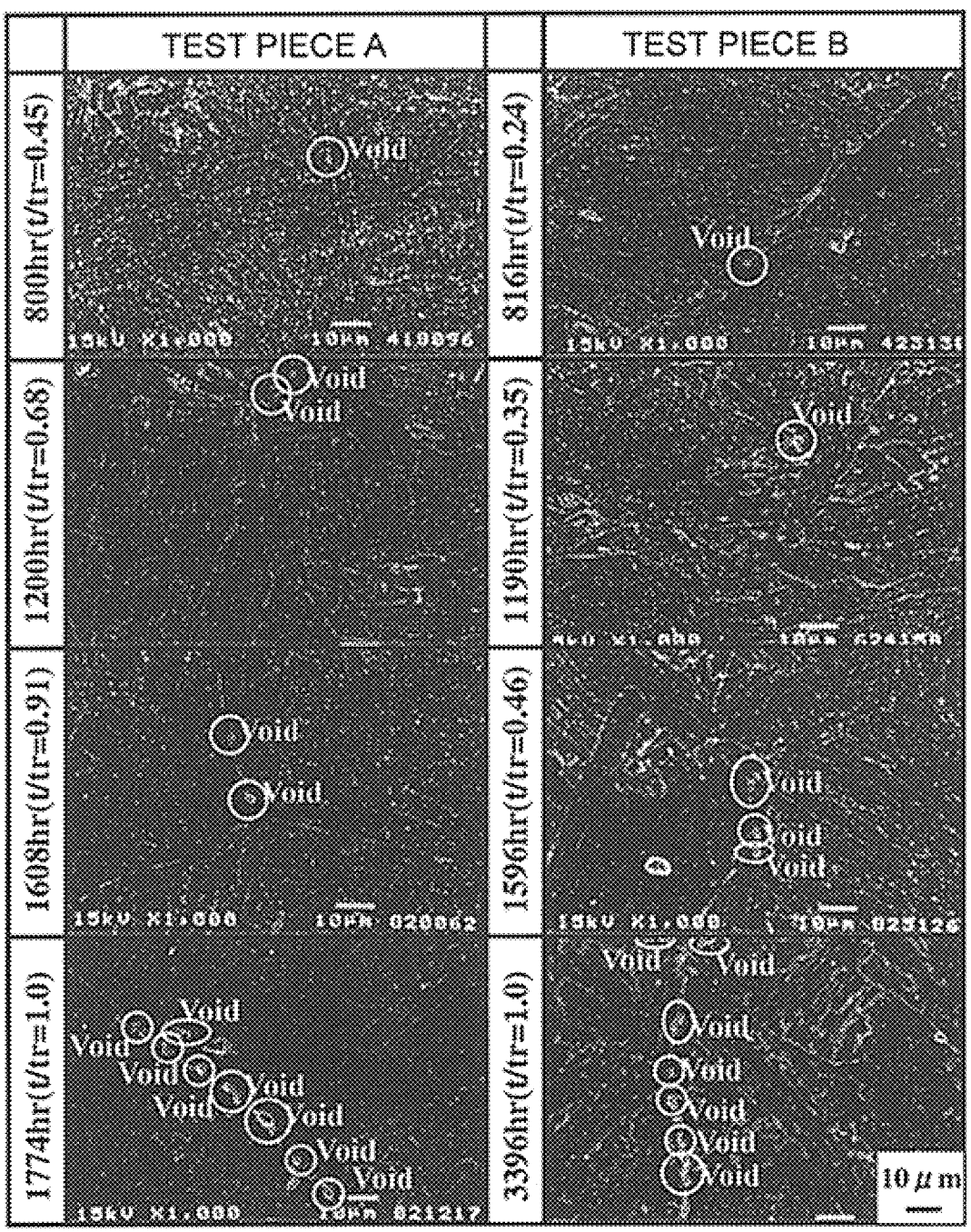
FIG. 6 is a scanning electron microphotograph showing a result of creep interruption test in the aforementioned test 1, in which ○ mark indicates a void.

FIG. 6 shows the void observation results of the test pieces A and B for the void growth behavior verification test using uniaxial creep rupture test piece of test 1. For the test piece A, a void of about 1 μm developed when the creep life consumption rate (t/tr)=0.45. When the creep life consumption rate (t/tr)=0.68, two voids of about 1 μm developed at one grain boundary, and when the creep life consumption rate (t/tr)=0.91, which is the last period of damage, two voids of about several microns developed at one grain boundary. When the creep life consumption rate (t/tr)=1.0, eight voids of about 5 μm developed at one grain boundary. For the test piece B, a void of about 1 μm developed when the creep life consumption rate (t/tr)=0.24. When the creep life consumption rate (t/tr)=0.35, one void of about 1 μm developed at one grain boundary, and when the creep life consumption rate (t/tr)=0.46, three voids of about several microns developed at one grain boundary. When the creep life consumption rate (t/tr)=1.0, five voids of about 5 μm developed at one grain boundary, and some of these voids were connected. The small void developing in the early period through the late period of damage had a low growth rate, and had a tendency to become larger just before the test piece was broken and to easily be connected and turn to a crack. Also, the void damage had a tendency to concentrate at a particular grain boundary.

[Result of Test 2]

Figure 7:
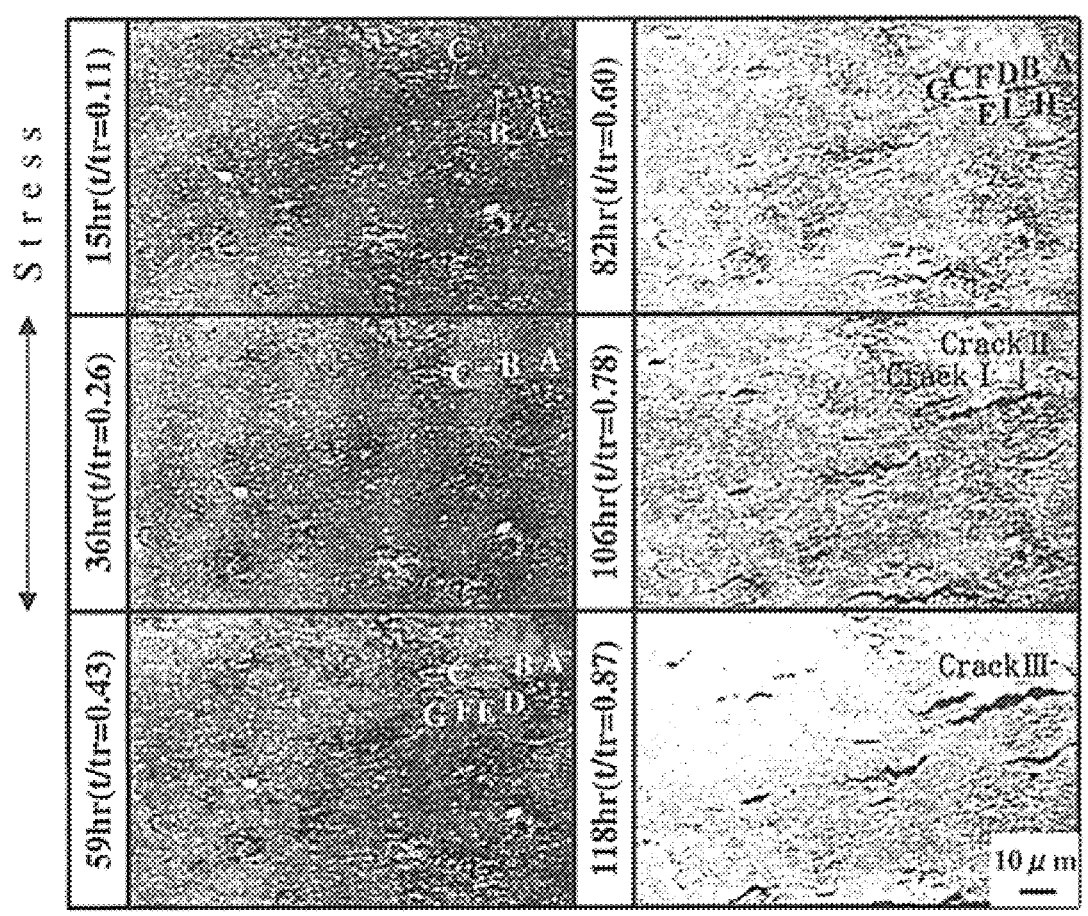
FIG. 7 is a scanning electron microphotograph showing a result of creep damage continuous observation test in the aforementioned test 2.

FIG. 7 shows the continuous observation results of creep damage in the same position of observation point ① of the test piece C using the SEM servo testing machine for the creep damage continuous observation test of test 2. At the observation point ①, when the creep life consumption rate (t/tr)=0.11, voids A, B and C developed at the same grain boundary, and when the creep life consumption rate (t/tr)= 0.26, the number of voids and the shape thereof were unchanged. However, when the creep life consumption rate (t/tr)=0.43, voids D, E, F and G developed at the same grain boundary, and when the creep life consumption rate (t/tr)= 0.60, voids H and I further developed, and the voids A, B, D, H and I began to connect with each other. When the creep life consumption rate (t/tr)=0.78, a crack II is generated by the connection of the voids A, B, D, H and I, and a crack I is generated by the connection of the voids E, F, C and G. When the creep life consumption rate (t/tr)=0.87, the cracks coalesced into a crack III.

At the observation point ②, when the creep life consumption rate (t/tr)=0.42, three voids developed, and when the creep life consumption rate (t/tr)=0.64, many-voids developed around the three voids. When the creep life consumption rate (t/tr)=0.77, connection was started, and when the creep life consumption rate (t/tr)=0.87, the connected voids grew into two cracks. As in the case of the aforementioned creep interruption test, the connection and the formation of microcrack proceeded at some crystal grain boundaries, and did not proceed at other crystal grain boundaries, and there was a tendency for the damage caused by the void to concentrate at a particular grain boundary.

[Result of Test 3]

Figure 8:
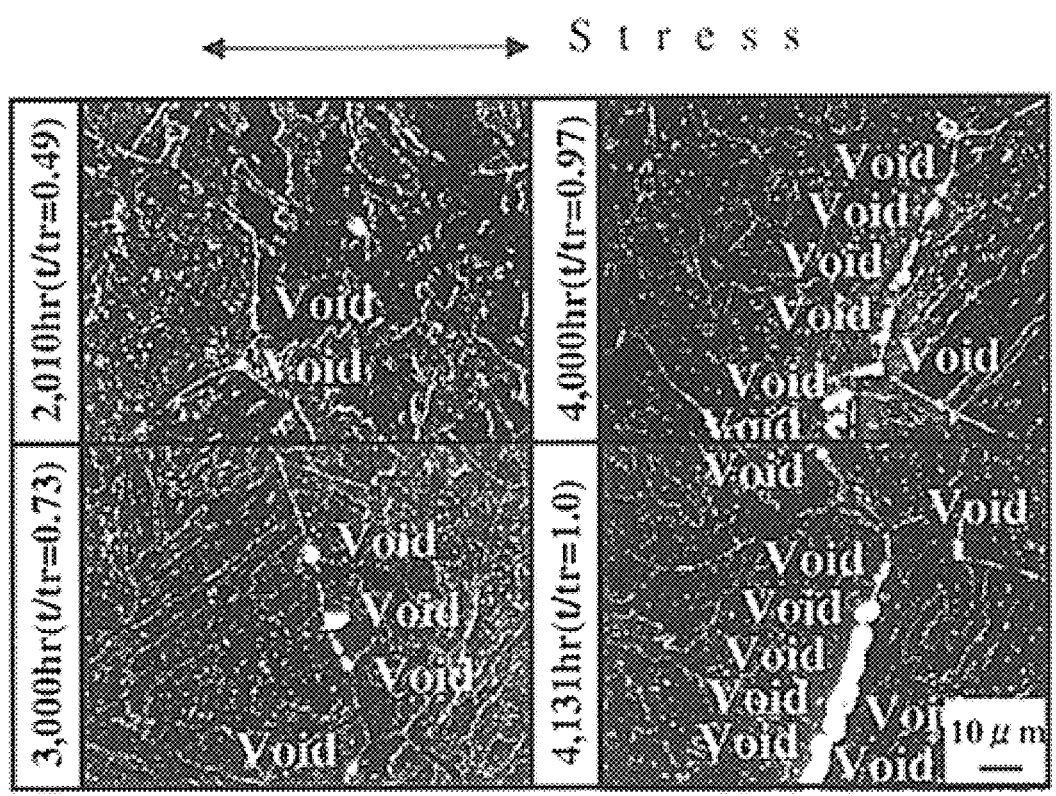
FIG. 8 is a scanning electron microphotograph showing a void form in welded joint portion in the aforementioned test 3.

FIG. 8 is a microphotograph typically showing a void form in welded joint portion in the pipe internal pressure creep test of test 3. The voids in the coarse grain Haz in the welded joint portion were larger in number and size than the voids in the coarse grain Haz reproduced material. Regarding the void development state, when the creep life consumption rate (t/tr)=0.49, voids of about 1 μm developed, and when the creep life consumption rate (t/tr)=0.73, a plurality of voids developed at the same grain boundary. When the creep life consumption rate (t/tr)=0.97, the connection of voids was found, and when the creep life consumption rate (t/tr)=1.0, a microcrack was formed.

Figure 9:
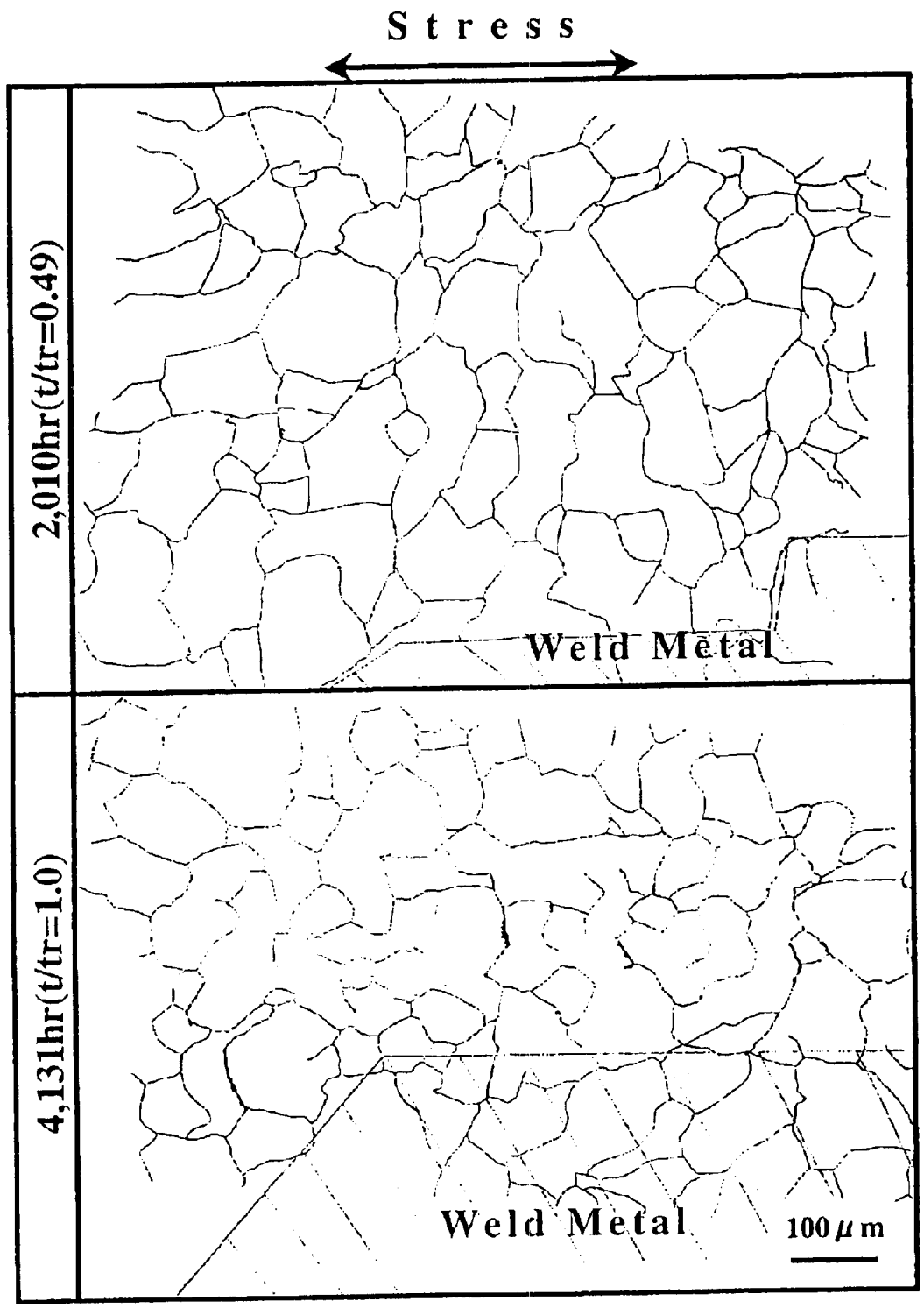
FIG. 9 is a view showing a void distribution state at the time of interruption in the aforementioned test 3.

FIG. 9 shows a void distribution state at the time of interruption (t/tr=0.49 and 1.0). When the creep life consumption rate (t/tr)=0.49, voids developed at random at the crystal grain boundary, and when the creep life consumption rate (t/tr)=0.73, the void development state was unchanged. When the creep life consumption rate (t/tr)=0.97, which is the last period of damage, a grain boundary at which voids connected was recognized, and when the creep life consumption rate (t/tr)=1.0, the connection of voids reached a length of one crystal grain boundary (microcrack). Regarding the growth of void along with the progress of damage, the same tendency as that in the uniaxial creep rupture test was recognized. From the above-described results, it was found that although a void develops at a grain boundary at random at first, a plurality of voids subsequently develop at a particular grain boundary, and some time later, they connect each other and develop into a microcrack.

[Result of Test 4]

Figure 10:
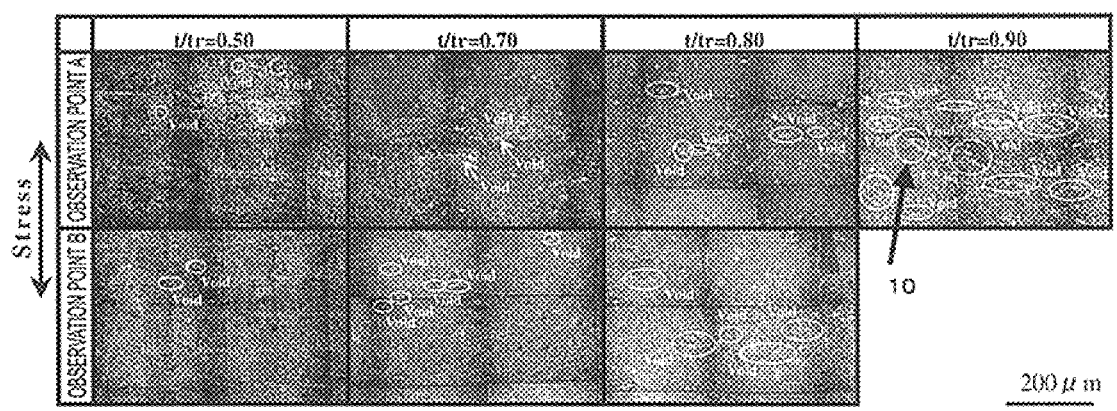
FIG. 10 is a scanning electron microphotograph showing a result of interruption replica observation in the aforementioned test 4.

FIG. 10 shows the results of interruption replica observation in the actual equipment acceleration test of test 4. When the creep life consumption rate (t/tr)=0.50, at both of the observation points A and B, there were grain boundaries at which one void developed at one crystal grain boundary, and the size of void was about several microns. When the creep life consumption rate (t/tr)=0.70, the number of grain boundaries at which a void developed increased, and at a particular grain boundary, some voids connected with each other. When the creep life consumption rate (t/tr)=0.80, the connection further proceeded. When the creep life consumption rate (t/tr)=0.90 at the observation point A, some connection length reached one grain boundary (microcrack). Reference numeral 10 in FIG. 10 denotes a portion of one grain boundary crack.

[Result of Test 5]

Figure 11:
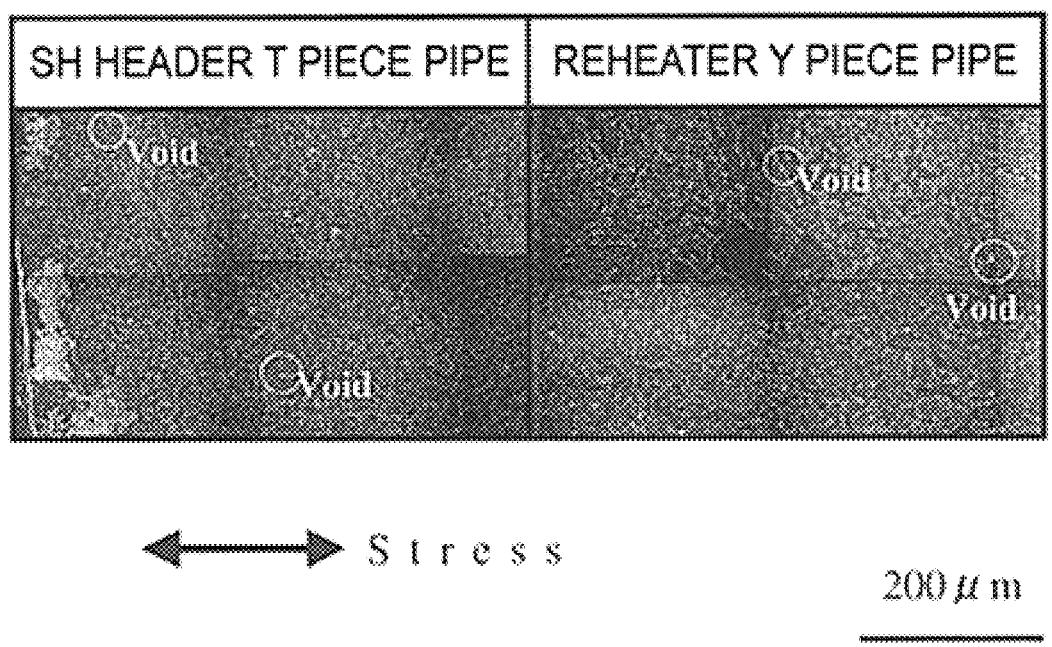
FIG. 11 is a scanning electron microphotograph showing an observation result of voids in actual equipment waste material, in which ○ mark indicates a void.

FIG. 11 shows the observation results of voids in actual equipment waste material of test 5. The creep life consumption rate (t/tr) of each equipment at the time of disposition, which was obtained by the creep rupture test, is given in Table 2.

TABLE 2

| | SH header T piece pipe | RHY piece pipe | RH header stub |
|---|---|---|---|
| Creep life consumption rate (t/tr) of boiler waste material | 0.204 | 0.137 | 0.0142 |

The number of voids developing in the actual equipment section (near the surface) was several, and voids that connected with each other and grew into a microcrack were not observed.

From the test results of tests 1 to 5, the development and growth behavior of void were studied. The grain boundary at which a void developed substantially intersected the direction of principal stress. The voids developed concentratedly at a particular grain boundary, and damage proceeded locally. This tendency was the same for the test piece and the actual equipment acceleration test result. From this result, it is thought that as long as the outer surface is concerned, for the creep damage, a particular grain boundary is first subjected to local damage in advance, and the damage incorporates with a nearby grain boundary crack just before the breakage.

Also, in each of the tests, there was a tendency for voids to develop and connect concentratedly at a particular grain boundary in the last period of damage. As a result of study on the cause therefor, the following can be considered.

(1) The intensity inherent in grain boundary, that is, a difference in orientation of crystal (surface energy) has relation.

(2) Three-dimensionally, the damage concentrates on the crystal surface perpendicular to the direction of principal stress.

(3) When a void develops, the stress distribution in the surroundings changes (Reference 9: Takayuki Kitamura, Ryuichi Ohtani, and Satoshi Nakayama, 42nd-term Scientific Lecture Meeting Proceedings, (1993), 25), and the void grows easily.

As the results of the tests, it was found that the development of void due to creep damage proceeds in a localized manner. Based on this damage behavior, a method in which for all of the grain boundaries at which a void develops in the observation field of view, the life is evaluated by using the maximum value of the ratio of void length to grain boundary length (void/grain boundary ratio) was used as the maximum void/grain boundary ratio (M parameter) method. This method provides the creep life evaluation method in accordance with the present invention.

Figure 12:
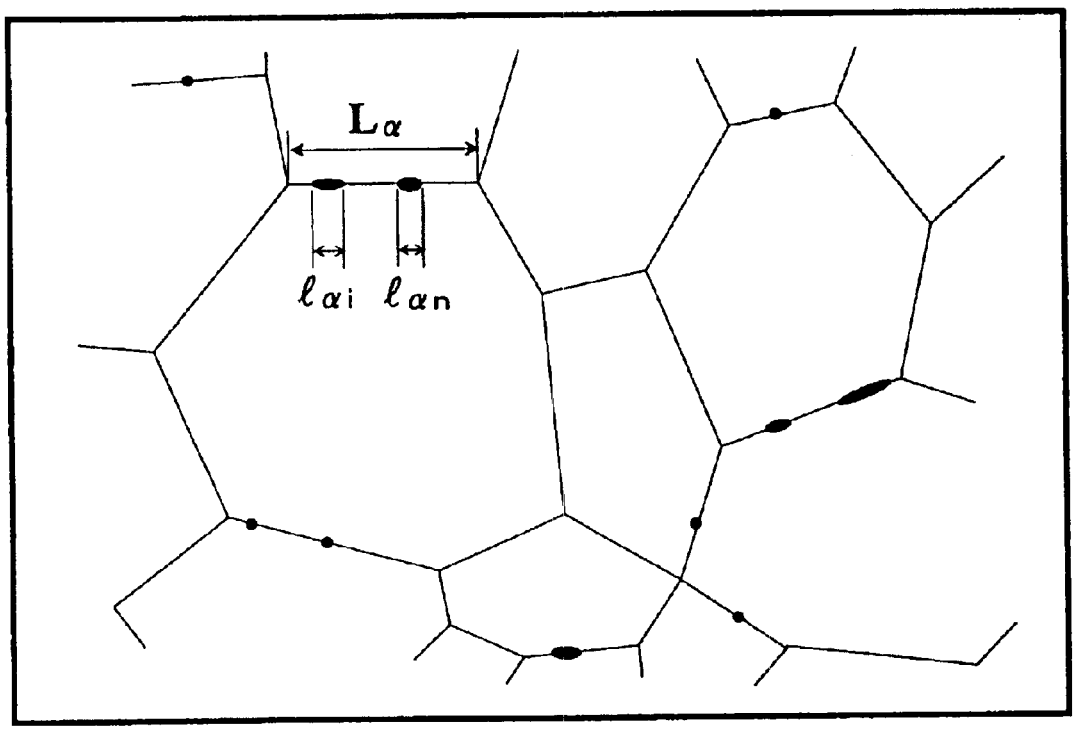
FIG. 12 is a view for illustrating the definition of M parameter (maximum void/grain boundary ratio) in accordance with the present invention.

FIG. 12 is a view for illustrating the definition of M parameter in the present invention. Reference character $L_\alpha$ denotes the total length of one grain boundary at which a creep void exists, n denotes the number of creep voids at a grain boundary having the total length of $L_\alpha$ of one grain boundary at which the creep voids exist, m denotes the number of grain boundaries at which a creep void exists, and $l_\alpha$ denotes a void length which is the length of the intersection of a grain boundary and a void along the grain boundary.

As seen from FIG. 12, the maximum void/grain boundary ratio (M parameter) is expressed by Equation 1.

$$\text{Maximum void/grain boundary ratio (MB)} = \underset{a=1}{\overset{m}{\text{MAX}}}\left[\frac{\sum_{i=1}^{n} l_{ai}}{L_a}\right] \quad \text{[Equation 1]}$$

Figure 13:
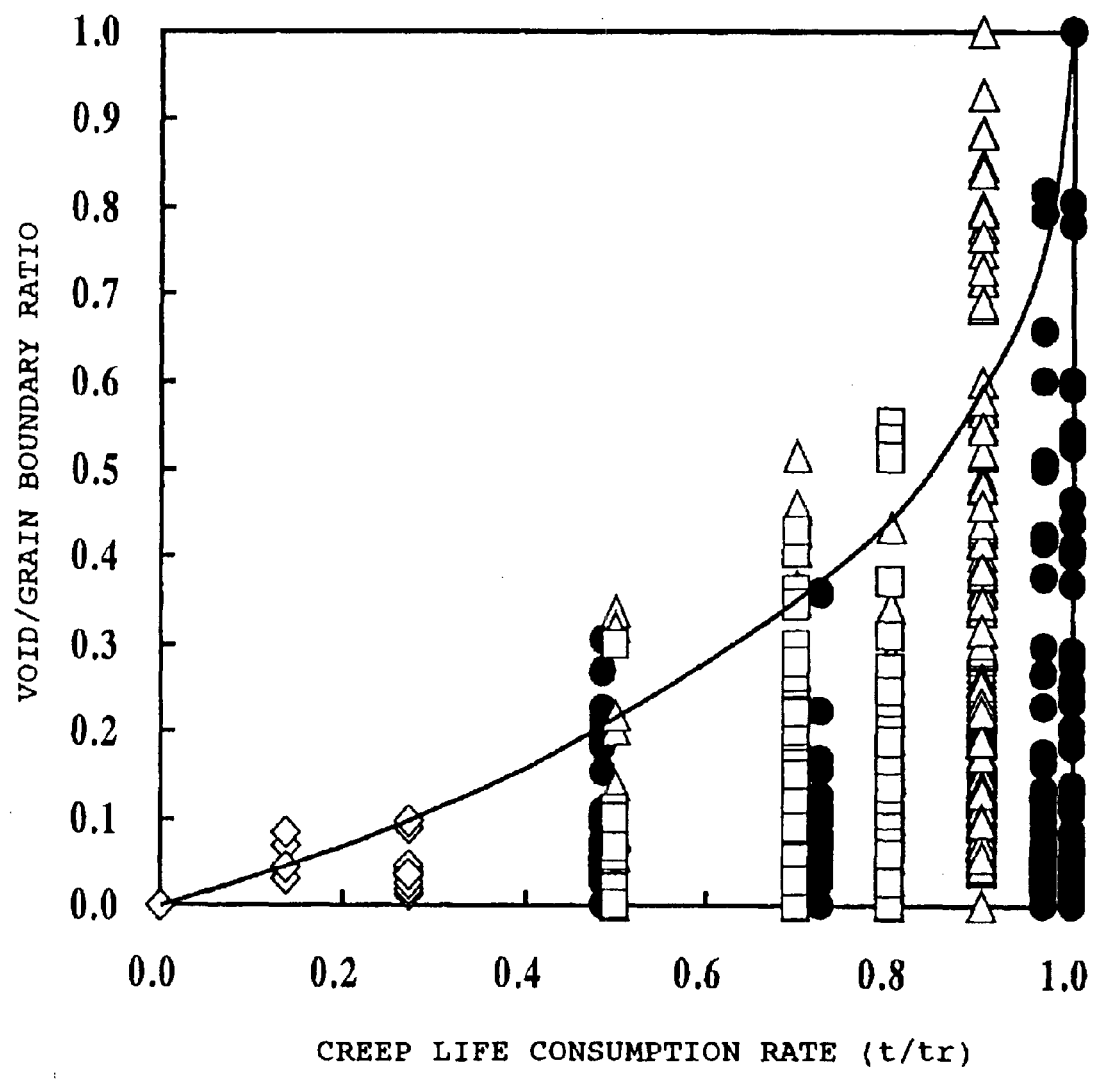
FIG. 13 is a graph showing a relationship between the void/grain boundary ratio obtained from the result of the aforementioned test and the creep life consumption rate (t/tr) obtained from the creep rupture test.
Figure 14:
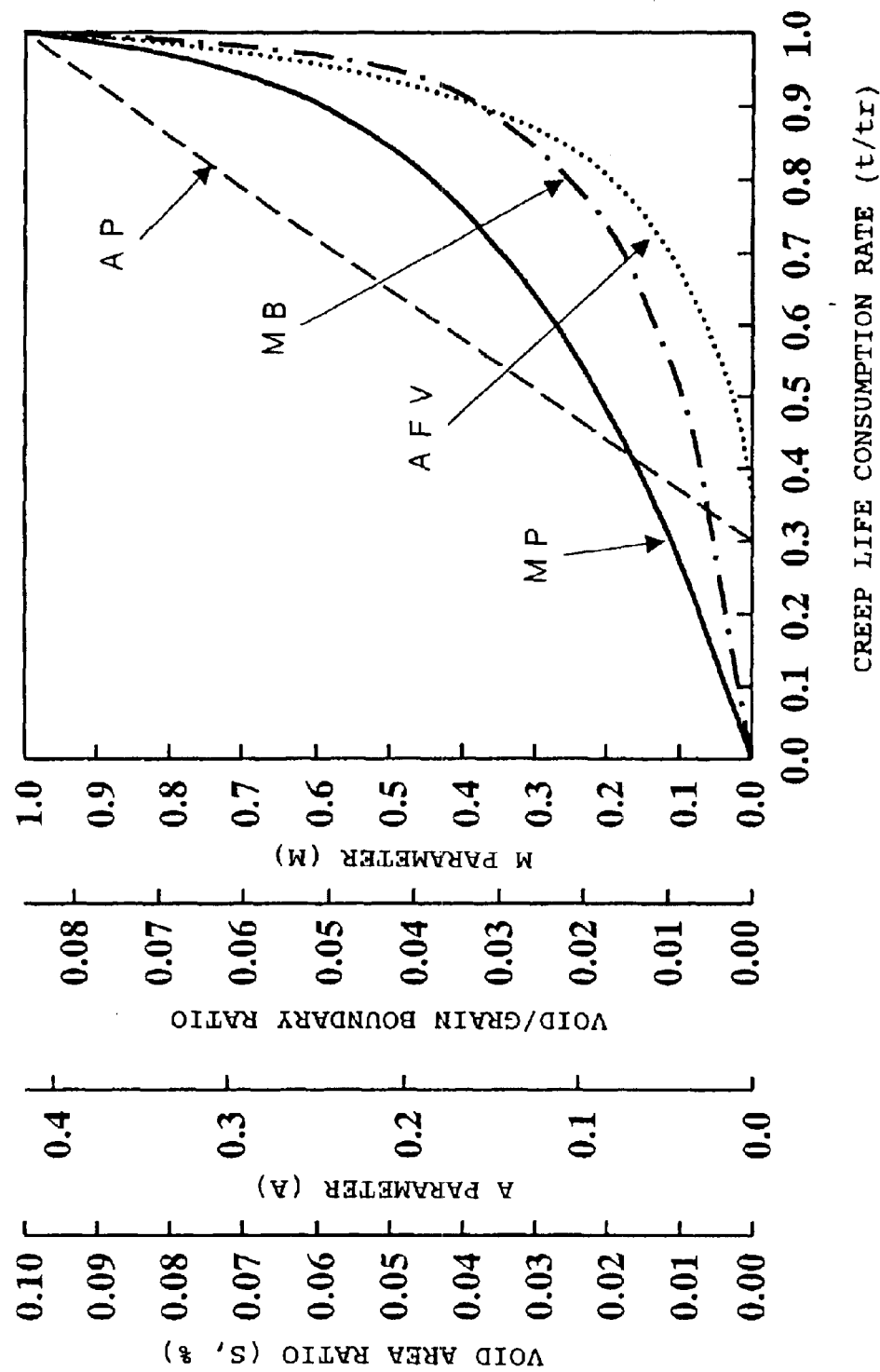
FIG. 14 is a graph showing a comparison between a master curve obtained by the M parameter (maximum creep void/grain boundary ratio) method according to the present invention and master curves obtained by the conventional parameter methods.

FIG. 13 is a graph showing a relationship between the void/grain boundary ratio obtained from the test result and the creep life consumption rate (t/tr) obtained from the creep rupture test. In the drawing, the solid line indicates an approximate curve of the maximum value of void/grain boundary ratio (master curve of M parameter method) in the result of pipe internal pressure creep test ● mark). Also, Δ mark indicates the creep test result at the observation point A of a high-temperature reheat steam pipe, □ mark indicates the creep test result at the observation point B of a high-temperature reheat steam pipe, and ◊ mark indicates the creep test result for the power plant boiler waste material. Until the creep life consumption rate (t/tr) reached 0 to 1.0, the M parameter showed a smooth curve that is convex downward, and an abrupt increase in parameter value in the last period of life as recognized in the conventional method (void area ratio method or void occupation ratio on grain boundary line method) as shown in FIG. 14 was not recognized. In FIG. 14, reference character MP denotes M parameter, AP denotes A parameter, MB denotes maximum void/grain boundary ratio, and AFV denotes void area ratio.

The features of parameter of the maximum void/grain boundary ratio (M parameter) method of the present invention are as follows:

(1) The growth and connection of voids proceed concentratedly at a particular grain boundary of the crystal grain boundaries in the coarse grain region of weld heat affected zone, and directly reflect the mechanism of crack formation, grow, and breakage.

(2) Although there are some variations, the M parameter has a good relation with the creep life consumption rate (t/tr) regardless of the wall thickness and the direction of weld line shown in FIG. 13.

Next, the sensitivity and accuracy between the present invention and the conventional method will be compared.

[Preparation of Master Curve]

FIG. 14 collectively shows master curves of the conventional methods (void area ratio method, A parameter method, void occupation ratio on grain boundary line method) using the pipe internal pressure creep test data. At this time, since the sensitivity and accuracy of the M parameter (maximum void/grain boundary ratio) method are checked under the same conditions, the master curve of conventional method, not the conventional master curve, was prepared by using the pipe internal pressure creep test data as in the case of the M parameter method.

The curve (or straight line) in FIG. 13 is the master curve used for life evaluation.

[Comparison of Sensitivity]

To confirm the sensitivity of the M parameter method, the master curve obtained by the M parameter method was compared with the master curve obtained by the conventional method (FIG. 14). In this specification, sensitivity is defined as a change rate of each parameter with respect to the creep life consumption rate. High sensitivity means a large gradient of graph in FIG. 14. The void area ratio method and the void occupation ratio on grain boundary line method have poor sensitivity in the early period of damage, but have higher sensitivity in the late period through the last period of damage. The A parameter method has high sensitivity from the middle period of damage. This is because a phenomenon that the number of damaged grain boundaries (a grain boundary having one or more voids is counted) increases in proportion to the creep life consumption rate is reflected. The M parameter method had the largest change among the methods from the early period of damage and showed a smooth curve that is convex downward until the last period of damage. The reason for this difference in behavior is thought to be that the void area ratio method and the void occupation ratio on grain boundary line method make evaluation using the average value in a certain evaluation area, so that the reaction in the early period of damage is minute, and the reaction takes place in the late period through the last period of damage in which the number of voids increases suddenly, while inversely the M parameter method makes evaluation by paying attention to the localized damage portion (that is, the maximum damage portion) only, so that the reaction takes place from the early period of damage.

[Comparison of Accuracy]

To confirm the accuracy of the M parameter method, a relationship between the creep life consumption rate (t/tr) obtained from the master curve of each parameter method and the creep life consumption rate (t/tr) obtained from the creep rupture test was studied. The data used are those indicated by the outline type marks (Δ, □, ◊, that is, actual equipment acceleration test and actual equipment waste material test data). The data indicated by the outline type marks represent each creep damage parameter value at the time of interruption (or at the time of disposition) in the test. From this damage parameter value, the creep life consumption rate was determined by using the master curve shown in FIG. 13. By comparing the creep life consumption rate obtained from each parameter method with the creep life consumption rate obtained from the rupture test (for the pipe internal pressure creep test and the actual equipment acceleration test, the ratio of interruption time to creep rupture time, and for the actual equipment waste material test, the ratio of operation time to total life obtained by adding operation time to future lifetime obtained from the creep rupture test), the accuracy was compared. The result is given in FIG. 15.

Figure 15:
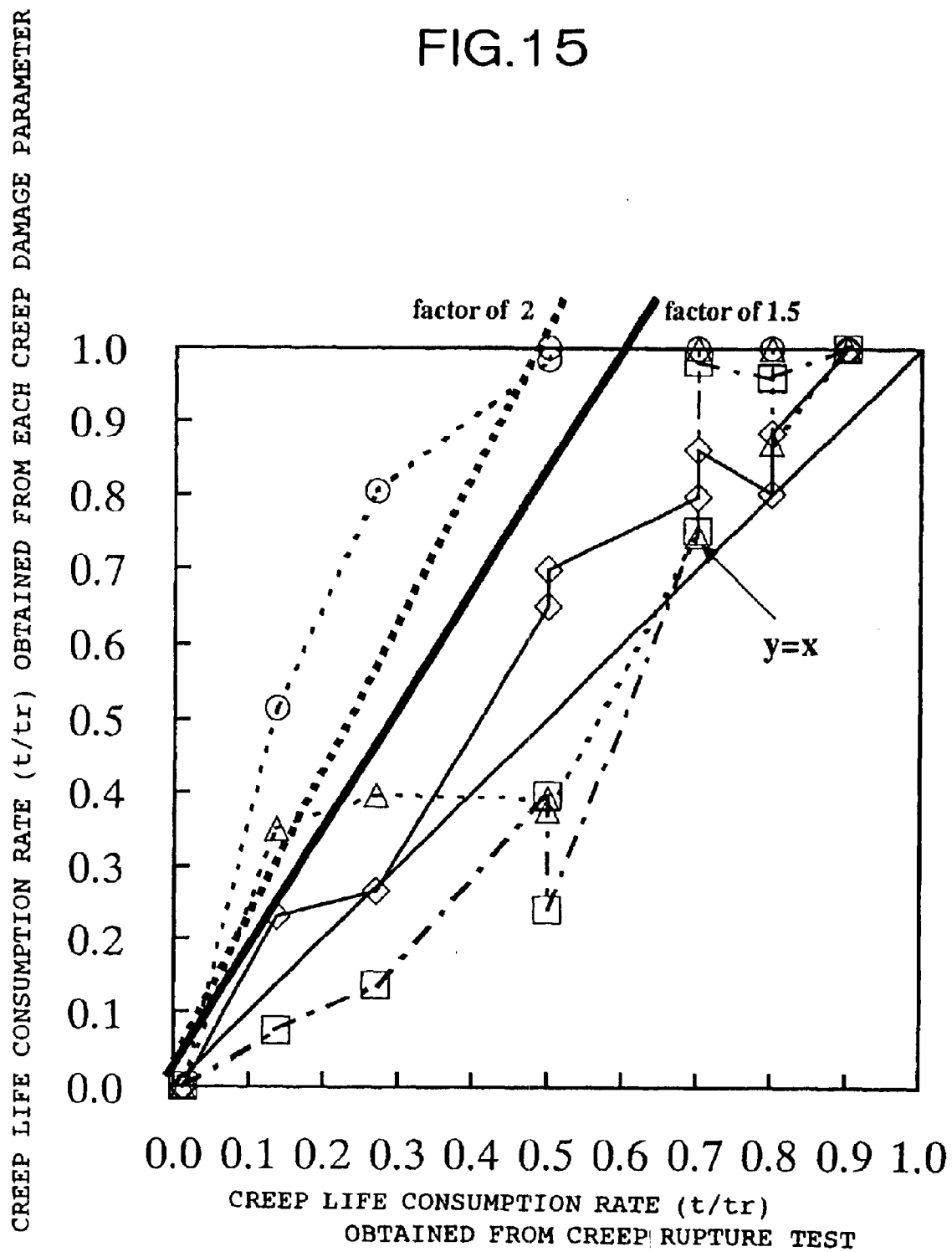
FIG. 15 is a graph showing the relationship between a creep life consumption ratio (t/tr) obtained by the M parameter method and the conventional method and a creep life consumption ratio (t/tr) obtained by the aforementioned creep rupture test.

FIG. 15 is a graph showing the relationship between the creep life consumption ratio (t/tr) obtained by the conventional method and the creep life consumption ratio (t/tr) obtained by the aforementioned creep rupture test. In the drawing, reference character F2 denotes a factor of 2, and F1.5 denotes a factor of 1.5. The ○ mark indicates the void area ratio, Δ mark indicates the A parameter, □ mark indicates the void/grain boundary ratio, and ◊ mark indicates the M parameter. Also, y=x in the drawing represents the fact that the creep life consumption rate obtained by each parameter method is equal to the creep life consumption rate obtained by the rupture test. In this test result, for all parameter methods, the creep life consumption rate thereof had the positive correlation with the creep life consumption rate obtained from the rupture test, approximately having an accuracy of a factor of 2. In particular, the M parameter method approximately had an accuracy of a factor of 1.5 as indicated by the thick solid line in FIG. 15.

Also, for the M parameter method, the curve is located always above y=x. That is to say, the evaluated creep life consumption rate is higher than that obtained by the rupture test. The M parameter method has a feature of making evaluation on the side of prudence because attention is given to the maximum damage portion (grain boundary always liable to develop into microcrack) only.

Also, a creep interruption test was conducted under various conditions by paying attention to the coarse grain region of weld heat affected zone of low alloy steel for boiler (2.25Cr-1Mo steel). Further, a study was performed on the possibility of precise estimation of the change in creep damage with time made by quantifying voids, including the result of actual equipment acceleration test. The main results obtained are as follows:

(1) The voids were scattered at random in the early period through the middle period of damage. After the middle period of damage, on the surface of member, the growth and connection of voids proceeded remarkably in advance at a particular grain boundary. That is, there was a tendency for the damage to proceed locally.

(2) Based on the development and growth behavior of voids, the "maximum void/grain boundary ratio (M parameter) method" for evaluating the maximum damage portion was newly invented.

(3) Paying attention to the fact that the creep damage proceeds locally on the outer surface, the voids were quantified by the "M parameter method", which was a local evaluation method. As the result of the rearrangement of the relationship with the creep life consumption rate (t/tr), a relationship in which data is distributed on a smooth curve that is convex downward regardless of the wall thickness and the direction of welding of an object to be evaluated was recognized. Also, a sudden rise in parameter value in the last period of damage, which was found in the void area ratio method and the void occupation ratio on grain boundary line method, was not recognized, and high sensitivity was exhibited from the early period to the last period of damage.

(4) Regarding a relationship between the creep life consumption rate (t/tr) obtained by the M parameter method and the creep life consumption rate (t/tr) obtained by the creep rupture test, approximately an accuracy of a factor of 1.5 was attained. Also, the M parameter method had a feature of making evaluation on the side of prudence because attention is given to the maximum damage portion only.

As described above, the M parameter method in accordance with the present invention is a new method of directly evaluating the maximum damage portion by reflecting the creep damage mechanism using voids in comparison with the conventional average damage evaluation method in an arbitrary area. As a result of the actual equipment acceleration test and the actual equipment waste material test under a multiaxial stress condition, the M parameter method has high sensitivity and accuracy, so that it is thought that this method can be applied satisfactorily to the life evaluation for actual equipment.

Industrial Applicability

According to the present invention, a person who is not skilled in actual equipment member can make evaluation of creep life consumption rate with high accuracy. Also, the creep life can be prolonged by a factor of about two at the maximum as compared with the conventional method.

Also, because of its simple configuration, the method can be automated by using picture processing, and thus the creep life consumption rate can be evaluated quickly with high accuracy. Therefore, the present invention is well worth using in industry.

What is claimed is:

1. A creep life evaluation method in which a creep life consumption rate of an equipment member subjected to deterioration due to the long-term use at high temperatures, said method comprising a first step of measuring the total length of a grain boundary at which a creep void exists and the void length of the creep void existing at the grain boundary, and a second step of obtaining a maximum creep void/grain boundary ratio (MB) on the basis of the results of said first step by Equation 1:

$$\text{Maximum creep void/grain boundary ratio (MB)} = \operatorname*{MAX}_{\alpha=1}^{m}\left[\frac{\sum_{i=1}^{n} l_{\alpha i}}{L_{\alpha}}\right]$$

In Equation 1, the $L_\alpha$ is a total length of one grain boundary at which a creep void exists, n is the number of creep voids at a grain boundary having the total length of $L_\alpha$ of one grain boundary at which the creep voids exist, m is the number of grain boundaries at which a creep void exists, and $l_\alpha$ is a void length of the intersection of a grain boundary and a void along the grain boundary.

* * * * *